United States Patent [19]

Weinstein et al.

[11] 3,954,970

[45] May 4, 1976

[54] ACTINOMYCIN COMPLEX FROM MICROMONOSPORA

[75] Inventors: Marvin J. Weinstein; Gerald H. Wagman, both of East Brunswick; Joseph A. Marquez, Montclair; Paul D. Watkins, Verona, all of N.J.

[73] Assignee: Schering Corporation, Kenilworth, N.J.

[22] Filed: May 24, 1974

[21] Appl. No.: 473,095

[52] U.S. Cl. ............................. 424/115; 195/80 R
[51] Int. Cl.² ........................................ A61K 35/00
[58] Field of Search ................... 424/115; 195/80 R

[56] References Cited
OTHER PUBLICATIONS

Miller, The Pfizer Handbook of Microbial Metabolites, McGraw-Hill Book Co., Inc., N.Y., N. Y., 1961, pp. 595 and 596.

*Primary Examiner*—Jerome D. Goldberg
*Attorney, Agent, or Firm*—Carver C. Joyner; Raymond A. McDonald; Stephen B. Coan

[57] ABSTRACT

An antibiotic complex consisting of about 25 components herein designated antibiotic 70591 complex is produced by *Micromonospora floridensis*, a novel microorganism. The antibiotic complex has been classified as an actinomycin and has been found to exhibit a broad spectrum of antibacterial activity.

3 Claims, No Drawings

ACTINOMYCIN COMPLEX FROM MICROMONOSPORA

This invention relates to the cultivation of a novel *actinomycete* and to the novel product elaborated thereby. More particularly, this invention relates to the production of a novel antibacterial composition herein designated antibiotic 70,591 complex by cultivating a novel species of *Micromonospora*, herein designated *Micromonospora floridensis* (sometimes also referred to as *M. floridensis*). The antibiotic complex (i.e. antibiotic 70,591 complex) consists of about twenty-five components which on the basis of physicochemical investigation have been classified as *actinomycins*.

The Microorganism

Macroscopic observations of *Micromonospora floridensis*, grown on a yeast extract-dextrose agar, shows fair growth with moderately plicate colonies having no aerial mycelia. The mycelia produced by the colonies range from about 0.4 to about 0.6 microns in diameter and bear spores on sympodially branched sporophores. On this medium a yellowish amber diffusible pigment is produced.

Microscopically, spores are observed which appear to be obovate to obpyriform with some spores appearing oblongelliptical to reniform. The spores measure about 0.8 microns in diameter and about 1.0–1.2 microns in length.

The following tables set forth the growth characteristics of *M. floridensis* on a variety of standard media, carbohydrate and nitrogen sources.

TABLE I

| Medium | Growth Characteristics |
| --- | --- |
| Czapeks Glucose Agar | Growth fair, raised, furrowed, no aerial mycelium, yellow diffusible pigment produced. g 4pg dark luggage tan, strong brown 55. |
| Asparagine-Glucose Agar | Growth fair, raised, granular, no aerial mycelium, light yellowish diffusible pigment produced. g2 pn dark brown, dark olive 108. |
| Ordinary Agar | Growth poor. |
| Nutrient Agar | Growth poor, flat, granular, no aerial mycelium, faint yellowish diffusible pigment produced. g4 ne luggage tan, strong brown 55. |
| Potato Plug | Growth good. |
| Peptone Glucose Agar | Growth poor. |
| Bennett's Agar | growth moderate, plicate, no aerial mycelium, dark greenish yellow diffusible pigment produced. gl ½ pn dark olive, dark grayish olive 111. |
| Emerson's Agar | Growth fair, furrowed, no aerial mycelium, yellowish diffusible pigment produced. g4pg dark luggage tan, strong brown 55. |
| Tomato Paste Oatmeal Agar | Growth good, raised, furrowed, no aerial mycelium, diffusible pigment not apparant. Very dark brownish black. |
| Glucose Yeast Extract Agar | Growth good, plicate, no aerial mycelium, dark yellow diffusible pigment produced. g5pe terra cotta, strong brown 55. |
| N Z Amine Dextrose Agar | Growth moderate, plicate, no aerial mycelium, amber diffusible pigment. g4pc russet orange, strong orange 50. |
| Czapek's Sucrose Agar (Scurose-Nitrate Agar) | Growth good, plicate, no aerial mycelium, dark amber diffusible pigment. g3pl clove Brown, light olive brown 94. |

TABLE II

| Medium | Growth Characteristics and Physical Properties |
| --- | --- |
| Loffler's Serum Medium (Difco) | Growth moderate, furrowed, g5 ne tile red, strong brown 55. Reaction: partial liquification. |
| Egg Agar (Dorset Egg Medium-Difco) | Growth poor. No Reaction. |
| Starch Agar | Growth fair, raised, no aerial mycelium, faint yellowish diffusible pigment produced. g4 pn chocolate brown, dark brown 59. |

TABLE II-continued

| Medium | Growth Characteristics and Physical Properties |
|---|---|
| | Hydrolysis: Positive. |
| Clacium Malate Agar | Growth fair, raised, granular, no aerial mycelium, no diffusible pigment apparent. black. Reaction: Negative. |
| Gelatin Medium | Growth fair to poor. Hydrolysis: Weak. |
| Tyrosine Medium (Melanin (Formation) | Growth poor, dark brownish amber diffusible pigment produced. Reaction: Positive. |
| Litmus Milk (Difco) | Milk not peptonized. |
| Cellulose Medium | Cellulose weakly decomposed. |
| Tyrosine Agar | Growth fair, granular, no aerial mycellium, dark reddish brown diffusible pigment abundantly produced. Hydrolysis: Positive. |
| Peptone Iron Agar ($H_2S$ Formation) | Growth moderate, plicate, no aerial mycelium, yellow diffusible pigment produced. g5nc burnt orange, strong reddish orange 35. Reaction: Negative. |
| Casein Agar | Growth fair, granular, no aerial mycelium, dark yellowish amber diffusible pigment produced. g51c copper, brownish orange 54. Hydrolysis: Positive. |
| Nitrate Reduction | Variable |
| Temperature | Grows at 26 and 37°C but not at 50°C. |
| Aerobic or Anaerobic | Aerobic. |

TABLE IV

CARBOHYDRATE UTILIZATION

| | Growth |
|---|---|
| Negative Control | poor |
| D-Arabinose | poor |
| L-Arabinose | moderate |
| Dulcitol | poor |
| D-Galactose | moderate |
| D-Glucose | moderate |
| Glycerol | poor |
| I-Inositol | poor |
| B-Lactose | moderate |
| D-Levulose | moderate |
| D-Mannitol | poor |
| Mannose | moderate |
| Melibiose | moderate |
| Melizitose | poor |
| Raffinose | poor |
| L-Rhamnose | poor |
| D-Ribose | moderate to poor |
| Salicin | poor |
| Sucrose | moderate |
| D-Xylose | moderate |

The foregoing cultural characteristics serve to distinguish *Micromonospora floridensis* from all previously described microorganisms. In addition to the foregoing, *Micromonospora floridensis* may also be distinguished by its production under aerobic fermentation conditions of a novel composition of matter, namely antibiotic 70,591 complex. Thus, the invention sought to be patented relates to *M. floridensis* as described above and to mutants and variants thereof capable of producing antibiotic 70,591 complex. *Micromonospora floridensis* has been deposited at the Northern Utilization Research and Development Division, U.S. Department of Agriculture, Peoria, Illinois and added to its culture collection as *M. floridensis* NRRL 8020.

Production of Antibiotic 70,591 Complex

*Micromonospora floridensis* produces Antibiotic 70,591 complex when cultivated in a nutrient containing assimilable sources of carbon and nitrogen. Substantial quantities of the antibiotic are produced when the microorganism is cultivated in an aqueous nutrient medium under submerged aerobic conditions. Exemplary of assimilable carbon sources are soluble starch, dextrose, sucrose, corn starch, lactose, potato starch, and cerelose. Exemplary of assimilable sources of nitrogen are proteins, amino acids and substances containing the same such as, beef extract, yeast extract, casein, egg yolk, tryptone, soybean meal, and the like. Specific examples of such nitrogen sources are set forth hereinabove under the heading Utilization of Nitrogen Sources. Good growth and antibiotic production may be obtained using the fermentation media and procedures set forth in the specific examples. The media may be supplemented with trace amounts of inorganic salts such as magnesium sulfate, ferrous sulfate, and especially, cobalt chloride to enhance antibiotic production. In general, the fermentation is conducted at a temperature range of from about 23°C to about 38°C with continuous aeration and continuous agitation at from about 250–400 rpm. Under these conditions, peak antibiotic production is attained in from about 2 to about 4 days. The pH of the fermentation is generally maintained in the range of from about 6.5 to about 8.3, preferably about 7.5. In small scale fermentations, e.g. 10 liters, it is usually not necessary to adjust the pH of the fermentation after inoculation. In large scale fermentations, however, it may be necessary to add materials to raise or lower the pH of the medium. These materials are those generally used in the art, e.g. dilute mineral acids, dilute alkali and alkaline earth metal hydroxides and carbonates and the like.

Generally, the fermentation is carried out in two or more stages, there being one or more germination stages followed by a fermentation stage. As a general rule, large (tank) fermentations utilize two germination stages whereas shake flask fermentations utilize a single germination stage.

During the course of the fermentation, especially after the first 36 hours, the fermentation is sampled, the sample subjected to serial dilution and disc tests against *Staphylococcus aureus* ATCC 6538P performed.

When peak antibiotic production is attained, the product is harvested, generally by methods known in the art, preferably by extraction with a water immiscible organic solvent such as, ethyl acetate, methylene chloride, chloroform; amylacetate, n-butanol, or the like. The extracts are combined, dried and concentrated to a residue in vacuo. The residue is redissolved in a suitable solvent, preferably methylene chloride and precipitated by the addition of a non-polar organic solvent such as hexane. The crude antibiotic complex obtained by this procedure is usually an orange-red amorphous solid.

Antibiotic 70591 is soluble in most polar organic solvents, absorbs ultraviolet light, has a characteristic infrared absorption spectrum and biological properties set forth herebelow which distinguish it from actinomycins known heretofore.

The antibiotic complex may be separated into about eleven groups by preparative thin layer chromatography on silica gel plates (silica gel GF 250 microns) using the lower phase of a solvent system composed of chloroform:methanol:water 2:1:1 as the developer. The groups are detected by observation of the color of the spot (orange-yellow to orange) or by bioautography against *S. aureus* ATCC 6538P. The groups are designated I-XI based upon their respective Rf values, group I being most distant from the origin with group XI being most proximate to the origin.

The groups are physically separated from each other by removing the silica gel from the plate in accordance with the respective RF values and subjecting each group to repetitive chromatography on silica gel using the above-described solvent system thereby obtaining each group in substantially pure form.

The groups are separated into the individual antibiotic 70591 components by preparative thin layer chromatography on silica gel using a solvent mixture composed of methylene chloride:acetone 7:3 as the developer. The individual components are detected by the appearance of colored bands, are isolated by removal of the individual bands from the plate and tested for antibacterial activity by bioautography against *S. aureus* ATCC 6538P. By this technique, it may be shown that groups I and II contain four components each, designated A through H. Groups III through VI contain three components each, said components being designated I through T. Groups VII throgh XI appear to contain only a single component, said components being designated S through Y.

Alternatively, by gradient elution of the silica gel column with acetone:methylene chloride the antibiotic 70591 complex may be separated into groups of components which groups may be further separated into individual antibiotic components by the procedure described immediately above. When the gradient elution technique is employed, the eluting solvent is initially composed of 5% acetone in methylene chloride, the solvent composition at the completion of the separation being about 55–60% acetone to about 40–45% methylene chloride. Eleven fractions are obtained (fractions O to X gradient) fraction O being first removed from the column. Fractions O g to III g contain inactive materials and are subordinate in importance to fractions IV g, V g, VI g and VII g which fractions contain the components found in Groups I through IV obtained by the above-described procedure. It is these fractions i.e. IV g  VII g i.e. components A through K that are especially useful as superinducers of interferon production by cells from animal tissue.

The Antibiotic Complex

The actinomycins represent a comprehensive class of antibiotics, however, they are reported to share a common phenoxazine nucleus to which is attached a plurality of amino or imino acids.

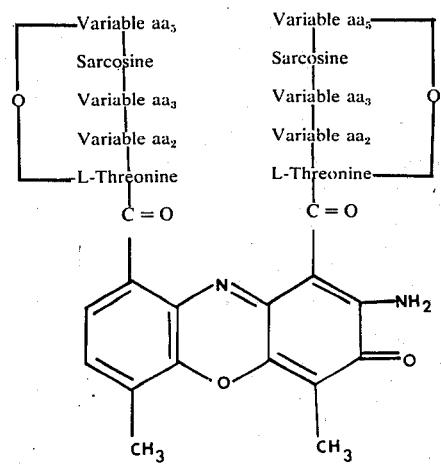

Wherein variable $aa_2$, $aa_3$ and $aa_5$ are amino or imino acids such as n-methyl valine, proline, valine, isoleucine or the like.

The antibiotics of this invention have been distinguished from the heretofore known actinomycins by comparison of their hydrolysis products with those of the known compounds. The comparisons are on the basis of high voltage electrophoresis (HVE) in one direction and ascending paper chromatography in a direction 90° to the first (analogous to two dimensional chromatography).

In order to ascertain the amino and imino acids comprising the peptide moiety of the antibiotic 70591 components and to differentiate then from known actinomycins, a sample of each of the antibiotic 70591 components was subjected to hydrolysis in screw-capped tubes containing 6N hydrochloric acid for three hours at 120°C. Susequent to being hydrolyzed, the individual components were subjected to high voltage electrophoresis at 4800 volts for 3 hours in 4% sodium formate buffered at pH 1.9 with formic acid using Whatman 3MM paper. This procedure was followed by ascending paper chromatography in a direction 90° from that of the electrophoresis. Chromatography was effected using a solvent mixture consisting of butanol:acetic acid: water (4:1:2). Detection for both procedures was effected by spraying with ninhydrin solution (0.2% ninhydrin in acetone). The location of the ninhydrin positive spots after the electrophoresis procedure was determined relative to that of sarcosine (1.00) and the location of the spots after chromatography was determined relative to the solvent front (Rf). The following table sets forth the results of the two procedures:

TABLE V

| Zone | Rsarc HVE | Rf PC | A HVE | A PC | B HVE | B PC | C HVE | C PC | D HVE | D PC | E HVE | E PC | F HVE | F PC | G HVE | G PC | H HVE | H PC | I HVE | I PC |
|---|---|---|---|---|---|---|---|---|---|---|---|---|---|---|---|---|---|---|---|---|
| Purple spot | 1.62 | 0.10 | | | | | | | | | | | | | | | | | + | + |
| Purple spot | 1.42 | 0.37 | | | | | | | | | | | | | | | + | + | | |
| Purple spot | 1.24 | 0.24 | | | | | | | | | | | | | | | | | | |
| Purple spot | 1.08 | 0.30 | | | | | | | | | | | | | | | | | | |
| Sarcosine | 1.00 | 0.26 | + | + | + | + | + | + | + | + | + | + | + | + | + | + | + | + | + | + |
| Yellow spot | 0.91 | | | | | | | | | | | | | | | | | | | |
| Valine | 0.88 | 0.46 | + | + | + | + | + | + | + | + | + | + | + | + | + | + | + | + | + | + |
| Purple spot | 0.89 | 0.21 | | | | | | | | | | | | | | | | | + | + |
| N-Me Alanine | 0.85 | 0.31 | | | + | + | | | | | + | + | + | + | + | + | + | + | + | + |
| Pink spot | 0.84 | 0.63 | | | | | | | + | + | | | | | + | + | + | + | | |
| Threonine | 0.82 | 0.24 | + | + | + | + | + | + | + | + | + | + | + | + | + | + | + | + | + | + |
| Proline | 0.80 | 0.34 | | | | | | | | | | | | | + | + | + | + | + | + |
| Purple spot | 0.74 | 0.21 | | | | | | | | | | | | | + | + | | | | |
| Yellow spot[1] | 0.74 | 0.44 | | | | | | | + | + | | | | | | | | | | |
| Yellow spot[2] | 0.71 | 0.28 | + | + | + | + | | | | | + | + | + | + | | | | | + | + |
| Purple spot | 0.73 | 0.59 | | | | | | | | | | | | | | | + | + | | |
| N-Me-Valine | 0.70 | 0.56 | + | + | + | + | + | + | + | + | + | + | + | + | + | + | + | + | + | + |
| Purple spot | 0.69 | 0.23 | | | | | | | | | | | | | | | | | | |
| Yellow spot | 0.65 | 0.23 | | | | | | | | | | | | | | | | | | |
| Pink spot | | 0.29 | | | | | | | | | | | | | | | | | | |
| Pink spot | 0.60 | 0.38 | | | | | | | | | + | + | | | | | | | | |
| Pink spot | 0.58 | 0.31 | | | | | | | | | | | | | | | | | | |
| Yellow spot[3] | 0.48 | 0.34 | | | | | + | + | + | + | + | | | | + | + | + | + | | |

| Zone | Rsarc HVE | Rf PC | J HVE | J PC | K HVE | K PC | L HVE | L PC | M HVE | M PC | N HVE | N PC | O HVE | O PC | P HVE | P PC | Q HVE | Q PC | R HVE | R PC |
|---|---|---|---|---|---|---|---|---|---|---|---|---|---|---|---|---|---|---|---|---|
| Purple spot | 1.62 | 0.10 | | | | | | | | | | | | | | | | | | |
| Purple spot | 1.42 | 0.37 | | | | | | | | | | | | | | | | | | |
| Purple spot | 1.24 | 0.24 | | | | | | | + | + | | | | | | | | | | |
| Purple spot | 1.08 | 0.30 | | | | | | | + | + | | | | | | | | | | |
| Sarcosine | 1.00 | 0.26 | + | + | + | + | + | + | + | + | + | + | + | + | + | + | + | + | + | + |
| Yellow spot | 0.91 | | | | | | + | | | | | | | | | | | | | |
| Valine | 0.88 | 0.46 | + | + | + | + | + | + | + | + | + | + | + | + | + | + | + | + | + | + |
| Purple spot | 0.89 | 0.21 | | | | | | | + | + | | | | | | | | | | |
| N-Me Alanine | 0.85 | 0.31 | + | + | + | + | + | + | | | | | + | + | + | + | + | + | + | + |
| Pink spot | 0.84 | 0.63 | | | + | + | | | | | | | + | + | + | + | | | | |
| Threonine | 0.82 | 0.24 | + | + | + | + | + | + | + | + | + | + | + | + | + | + | + | + | + | + |
| Proline | 0.80 | 0.34 | + | + | + | + | + | + | + | + | | | + | + | + | + | | | | |
| Purple spot | 0.74 | 0.21 | | | | | | | +(.31) | | | | | | | | | | | |
| Yellow spot[1] | 0.74 | 0.44 | | | | | + | + | + | + | + | + | | | | | | | + | + |
| Yellow spot[2] | 0.71 | 0.28 | + | + | | | | | | | + | + | | | | | | | | |
| Purple spot | 0.73 | 0.59 | | | | | | | + | + | + | + | + | + | | | + | + | | |
| N-Me-Valine | 0.70 | 0.56 | + | + | + | + | + | + | + | + | + | + | | | + | + | | | + | + |
| Purple spot | 0.69 | 0.23 | | | | | | | | | | | | | | | | | + | + |
| Yellow spot | 0.65 | 0.23 | | | | | | | | | | | | | | | | | | |
| Pink spot | | 0.29 | | | | | | | | | | | | | | | | | | |
| Pink spot | 0.60 | 0.38 | | | | | | | | | | | | | | | | | | |
| Pink spot | 0.58 | 0.31 | | | | | | | | | + | + | | | | | | | | |
| Yellow spot[3] | 0.48 | 0.34 | | | + | + | | | | | + | + | + | + | + | + | + | + | + | + |

| Zone | Rsarc HVE | Rf PC | S HVE | S PC | T HVE | T PC | U HVE | U PC |
|---|---|---|---|---|---|---|---|---|
| Purple spot | 1.62 | 0.10 | | | | | | |
| Purple spot | 1.42 | 0.37 | | | | | | |
| Purple spot | 1.24 | 0.24 | | | | | | |
| Purple spot | 1.08 | 0.30 | | | + | + | + | + |
| Sarcosine | 1.00 | 0.26 | + | + | + | + | + | + |
| Yellow spot | 0.91 | | | | | | | |
| Valine | 0.88 | 0.46 | + | + | + | + | + | + |
| Purple spot | 0.89 | 0.21 | | | | | | |
| N-Me Alanine | 0.85 | 0.31 | + | + | + | + | + | + |
| Pink spot | 0.84 | 0.63 | + | + | | | + | + |
| Threonine | 0.82 | 0.24 | + | + | + | + | + | + |
| Proline | 0.80 | 0.34 | | | | | + | + |
| Purple spot | 0.74 | 0.21 | | | | | | |
| Yellow spot[1] | 0.74 | 0.44 | + | + | + | + | + | + |
| Yellow spot[2] | 0.71 | 0.28 | + | + | + | + | + | + |
| Purple spot | 0.73 | 0.59 | | | | | | |
| N-Me-Valine | 0.70 | 0.56 | + | + | + | + | + | + |
| Purple spot | 0.69 | 0.23 | | | | | | |
| Yellow spot | 0.65 | 0.23 | | | | | + | + |
| Pink spot | | 0.29 | | | + | | | |
| Pink spot | 0.60 | 0.38 | | | | | | |
| Pink spot | 0.58 | 0.31 | | | | | | |
| Yellow spot[3] | 0.48 | 0.34 | + | + | + | + | + | + |

[1,2,3]Imino acid

The components of the antibiotic 70591 complex have as constituent parts both known amino and imino acids and amino and imino acids which have not heretofore been shown to be constituents of actinomycin antibiotics. In the preceding table (Table V) the plus (+) signs represent the location of the amino and imino acids comprising the peptide moiety of antibiotic 70591. The known acids are named and those whose identities have not been unequivocally established are designated by their respective locations after high voltage electrophoresis and paper chromatography of hydrolysates of the respective components. They are also identified by the color produced with ninhydrin. All of the components contain sarcosine, valine and threonine. Components B, E through L, and O through U also have N-methyl alanine. Components G through M, O, P, and U also have proline. N-methyl valine may be isolated from all components except components O and Q.

Antibiotic 70591 complex is active against certain gram-positive and gram-negative bacteria, and is also active against certain fungi. Tables VI and VII set forth below evidence such activity.

Table VI

In Vitro Activity of Antibiotic 70591 Complex in Mueller-Hinton Broth pH 7.4

| Organism | Antibiotic 70591 Complex |
|---|---|
| Staphylococcus aureus 209 P | 0.3 |
| 12 | 0.3 |
| Streptococcus pyrogenes C | 0.1 |
| Escherichia coli Sc | >10 |
| Pseudomonas aeruginosa Sc | 3.0 |
| Candida albicans | 0.1 |
| Trichophyton mentagrophytes | >10 |

The antibiotic 70591 complex and the individual members thereof are antibacterial agents and thus may be used in vitro for disinfecting hospital toilets, bidets, floors and stairways and the like. They may also be used as bacteriostatic agents for cages housing laboratory animals. Additionally, the antibiotic 70591 complex may be used in oils (e.g. motor oils) and paints, particularly latex based paints as a preservative. However, antibiotic 70591 complex is not limited to utility as an antibacterial agent but may also be used as a superinducer in the preparation of interferon from cells from animal tissue. Some of the components of the antibiotic complex (i.e. components A through K inclusive) exhibit a substantially higher degree of superinduction than does a known superinducer, actinomycin D. The method employed for superinduction of interferon is substantially like that described by Havell and Vilcek, Antimicrobial Agents and Chemotherapy (1972) Vol. 2, No. 6 Page 476–484.

In general, the procedure involves the addition of interferon inducers such as a mixture of polyinosinic acid, polycyclic acid (Poly I, Poly C) to cultures of cells from animal tissue. The interferon produced by the inducers is assayed by the method of Wagner, R.R., Bacteriological Rev. 24, (1960). After assaying for interferon the compounds of this invention are added and, after a suitable incubation period substantially increased titers of interferon are obtained.

The following examples set forth the best mode for practicing this invention. However the process aspect thereof is not limited to the specific conditions set forth but are to be construed as exemplary rather than limiting.

Example 1

Tank Fermentation of Micromonospora Floridensis

A. Germination Stage

Inoculate a series of 300 ml. flasks each containing 100 ml. of sterile medium (see Medium A below) with a loopful of *M. floridensis* from an agar slant or with 5 ml. of an actively growing culture. Incubate the flasks with continuous agitation for from about 2 to about 4 days until vigorous growth is obtained. The incubation is preferably conducted with continuous rotary agitation at about 250 to 300 rpm at about 28°C.

B. Second Germination Stage.

Transfer 25 ml. of the inoculum prepared in step A to a series of 2 liter Erlenmeyer flasks containing 500 ml. or sterile Medium A. Incubate this medium with rotary agitation as described in step A, preferably at 28°C for about 72 hours or until vigorous growth is obtained.

C. Fermentation Stage

Transfer 500 ml. of the germinated culture to each of a series of 14 liter fermentors containing 9.5 liters of fermentation Medium (see Medium B below) and ferment the mixture with agitation at from about 200 to about 500 rpm, preferably about 400 rpm, at a temperature in the range of 26°C to 38°C preferably at about 28°–30°C, and with aeration at about 3 to 5 liters/minute. Sample the fermentation at convenient intervals after the first 24 hours, continue the fermentation until peak antibiotic activity is attained as determined by Table VII In Vitro Antibacterial Activity of Antibiotic 70591 Complex

| Concentration per ml | S. aureus | S. pyrogenes | B. subtilis Zone Diameter - mm | E. coli | Ps. aeruginosa Disc Diameter - mm | C. albicans |
|---|---|---|---|---|---|---|
| Complex | | | | | | |
| 1000 ug | 18 | 18 | 17 | ± | 10 | ± |
| 100 ug | 15 | 15 | 15 | 0 | 0 | 0 |
| 10 ug | 9 | 8 | 8 | 0 | 0 | 0 |
| Component V | | | | | | |
| 1000 ug | 21 | 21 | 23 | ± | 12 | ± |
| 100 ug | 20 | 19 | 17 | 0 | 0 | 0 |
| 10 ug | 11 | 9 | 15 | 0 | 0 | 0 |
| Component VI | | | | | | |
| 1000 ug | 21 | 20 | 22 | ± | 10 | ± |
| 100 ug | 17 | 11 | 15 | 0 | 0 | 0 |
| 10 ug | 12 | 12 | 11 | 0 | 0 | 0 | disc tests against *S. aureus* ATCC 6538P and harvest the antibiotic mixture as described in Example 2.

| Garmination Medium | Medium A |
|---|---|
| A germination medium of the following composition was used for both primary and secondary germinations: | |
| Beef extract | 3 g |
| Tryptone | 5 g |
| Dextrose | 1 g |
| Potato starch | 24 g |
| Yeast extract | 5 g |
| $CaCO_3$ | 2 g |
| $H_2O$ (Tap) | 1000 ml |
| (adjust to pH 7.5 with NaOH before sterilizing) | |
| Fermentation Medium | Medium B |
| A useful fermentation medium for production of antibiotic by *M. floridensis* follows: | |
| Soluble starch | 20 g |
| Yeast extract | 8.75 g |
| NZ-amine | 5 g |
| Dextrose | 10 g |
| $CaCO_3$ | 4 g |
| $H_2O$ (Tap) | 1000 ml |
| Adjust to pH 7.5 and maintain between pH 6.5 and 8.3 throughout the fermentation. | |

Example 2

Isolation of Antibiotic 70591 Complex

Adjust the fermentation medium to about pH 6.5 and extract repeatedly with ethyl acetate until the broth is substantially free of antibiotic activity. Combine the extracts and concentrate to a residue in vacuo. The antibiotic complex so obtained has the following physicohemical properties:

Table VIII

| Ultraviolet absorption: | |
|---|---|
| Wavelength m$\mu$ | 1% 1cm (methanol) |
| 216 | 246 |
| 243 | 201 |
| 448 | 154 |

TABLE IX

| Infrared absorption — Characteristics peaks; Wavelength microns | |
|---|---|
| 3.09 (m) | 7.67 (m) |
| 3.40–3.50 (Nujol) | 7.87 (m) |
| 5.71 (m) | 8.18 (sh) |
| 5.90 (sh) | 8.37 (m, brd.) |
| 6.02 (vs,brd.) | 9.15 (m, brd.) |
| 6.08 (sh) | 9.40 (m) |
| 6.14 (sh) | 10.10 (w) |
| 6.30 (s) | 10.53 (w) |
| 6.60 (m) | 11.42 (w) |
| 6.85 (Nujol) | 12.20 (w, brd.) |
| 7.25 (Nujol) | 13.87 (w, brd.) |

Notations:
vs-very strong; s-strong; m-medium; w-weak; brd-broad; sh-shoulder

Amino and imino acid constituents; sarcosine, valine, N-methyl valine, threonine, proline, N-methyl alanine and others not yet identified.

Example 3

Partial Separation of Antibiotic 70591 Complex

Dissolve the residue from Example 2 in the lower phase of a solvent system composed of chloroform:methanol:water (2:1:1) and chromatograph on silica gel GF 250 microns plates using the aforedescribed solvent system as the developer. The following groups of product are obtained from a 1 gram charge:

TABLE X

| Group | Rf | Yield (mg.) |
|---|---|---|
| I | 0.70 | 3.4 |
| II | 0.68 | 3.8 |
| III | 0.65 | 6.3 |
| IV | 0.64 | 4.0 |
| V | 0.62 | 11.0 |
| VI | 0.48 | 19.0 |
| VII | 0.44 | 13.0 |
| VIII | 0.42 | 7.0 |
| IX | 0.40 | 13.0 |
| X | 0.37 | 31.0 |
| XI | 0.10 | 45.0 |

Example 4

Partial Separation of Antibiotic 70591 Complex

Prepare a 4 × 40 inches chromatographic column containing 184 g of silica gel $GF_{254}$ (E. Merck) using 5% acetone in methylene chloride as the solvent system. Dissolve 1.4 g of antibiotic 70591 complex in 10 ml of acetone add to the botton of the column while maintaining the temperature of the column at 4°C. Run the chromatography in an ascending manner by pumping the eluting solvent through the absorbent from the bottom while taking off 5 ml fractions from the top. Monitor the column by thin layer chromatography (in duplicate) using the lower phase of a chloroform:methanol:water mixture (2:1:1), detection of the components being effected by spraying the thin layer plate with a sulfuric acid:methanol mixture (1:1) followed by heating and exposure to iodine vapors. Change the gradient by increasing the concentration of acetone in the eluting solvent as required to remove the components (i.e. from 5% to about 55–60%). Perform a confirmatory bioautogram by plating the duplicate against *Staphylococcus aureus* 209P. Using this procedure, a separation is obtained substantially as follows:

TABLE XI

| Fraction | Eluate Volume | Fraction | Eluate Volume |
|---|---|---|---|
| 0 g* | 400 ml. | V g | 160 ml. |
| I g | 90 ml. | VI g | 220 ml. |
| II g | 160 ml. | VII g | 60 ml. |
| III g | 80 ml. | VIII g | 110 ml. |
| IV g | 80 ml. | IX g | 290 ml. |
| | | X g | 680 ml. |

*g = gradient

Example 5

Separation of Antibiotic 70591 Components

Dissolve each of the eleven groups of antibiotic in a solvent mixture consisting of methylene chloride:acetone (7:3). Re-chromatograph on individual silica gel plates using the solvent mixture just described as the developer. The groups are further separated in the manner set forth below as determined by bioautography against *S. aureus* ATCC 6538P. The relative activity of the individual component against the organism being as set forth:

TABLE XII

| Group | Component | Activity |
|---|---|---|
| I | A | +++ |
| | B | +++ |
| | C | +++ |
| | D | +++ |
| II | E | +++ |
| | F | +++ |

TABLE XII-continued

| Group | Component | Activity |
|---|---|---|
|  | G | +++ |
|  | H | +++ |
| III | I | +++ |
|  | J | +++ |
|  | K | +++ |
| IV | L | +++ |
|  | M | +++ |
|  | N | + |
| V | O | + |
|  | P | +++ |
|  | Q | +++ |
| VI | R | +++ |
|  | S | +++ |
|  | T | + |
| VII | U | ++ |
| VIII | V | ++ |
| IX | W | ++ |
| X | X | ++ |
| XI | Y | ++ |

We claim:

1. A process for preparing Antibiotic 70591 complex which comprises cultivating *Micromonospora floridensis* NRRL 8020 under submerged aerobic conditions in an aqueous medium containing assimilable sources of nutrient materials until a complex having substantial antibacterial activity is produced and isolating the antibiotic 70591 complex from the medium.

2. A process for preparing Antibiotic 70591 complex according to claim 1 wherein Micromonospora floridensis NRRL 8020 is cultivated at a temperature of from about 26° to about 38°C and at a pH within the range of 6.5 to 8.3.

3. Antibiotic 70591 complex obtained by the process of claim 1, said antibiotic complex having ultraviolet absorption maxima at about 216, 243 and 448 m$\mu$ with an $\Sigma 1cm(CH_3OH)^{1\%}$ of 246, 201 and 154, respectively; having an infrared absorption spectrum substantially as set forth in Table IX said antibiotic 70591 complex being characterized as having antibacterial activity substantially set forth in Table VI; and being further characterized as having antibacterial activity substantially as set forth in Table VII.

* * * * *